United States Patent [19]
Krenzer et al.

[11] 3,982,922
[45] Sept. 28, 1976

[54] HERBICIDAL COMPOSITIONS CONTAINING FURANCARBOXAMIDES

[75] Inventors: John Krenzer, Oak Park; Sidney B. Richter, Chicago, both of Ill.

[73] Assignee: Velsicol Chemical Corporation, Chicago, Ill.

[22] Filed: Feb. 12, 1971

[21] Appl. No.: 115,077

Related U.S. Application Data

[62] Division of Ser. No. 694,075, Dec. 28, 1967, abandoned.

[52] U.S. Cl............................... 71/88; 260/347.3; 424/285
[51] Int. Cl.² ........................................ A01N 9/00
[58] Field of Search ................................ 71/88, 118

[56] References Cited
UNITED STATES PATENTS

| | | | |
|---|---|---|---|
| 3,277,107 | 10/1966 | Neighbors | 71/118 |
| 3,288,851 | 11/1966 | Martin et al. | 71/118 |
| 3,290,374 | 12/1966 | Kraiman et al. | 71/118 |
| 3,352,663 | 11/1967 | Freund et al. | 71/88 |

*Primary Examiner*—Glennon H. Hollrah
*Attorney, Agent, or Firm*—Robert J. Schwarz; Dietmar H. Olesch

[57] ABSTRACT

A compound of the formula:

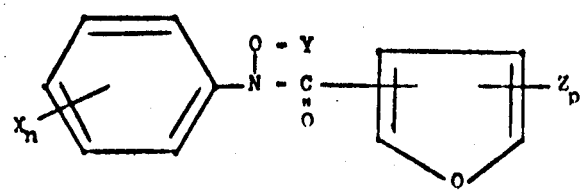

wherein $n$ is an integer of from 1 to 3; X is selected from the group consisting of halogen, an aliphatic radical, nitro, hydroxy, alkoxy, acyl, acyloxy and cyano; Y is selected from the group consisting of hydrogen, alkyl, acyl, alkoxycarbonyl, alkylthiocarbonyl, alkoxycarbonylalkylene, and a carbamoyl radical; Z is selected from the group consisting of halogen, alkyl, alkoxy and nitro; and p is an integer of from 0 to 3.

1 Claim, No Drawings

HERBICIDAL COMPOSITIONS CONTAINING FURANCARBOXAMIDES

This application is a division of application Ser. No. 694,075, filed Dec. 28, 1967, now abandoned.

This invention relates to new compounds and to pesticidal compositions containing such compounds as well as to methods of utilizing such compositions to control pests.

The compounds of this invention can be represented by the following formula:

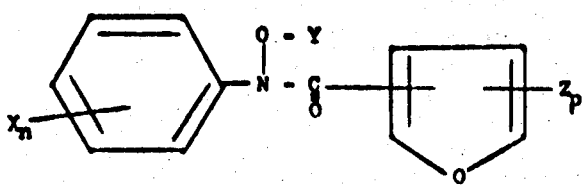

(I)

wherein n is an integer of from 1 to 3; X is selected from the group consisting of a halogen, an aliphatic radical, nitro, hydroxy, alkoxy, acyl, acyloxy and cyano; Y is selected from the group consisting of hydrogen, alkyl, acyl, alkoxycarbonyl, alkylthiocarbonyl, alkoxycarbonylalkylene, and a carbamoyl radical; Z is selected from the group consisting of a halogen, alkyl, alkoxy and nitro; and p is an integer of from 0 to 3; and, when n or p is greater than one, X or Z can be the same or different.

In a preferred class of the compounds represented by the above formula, the furyl ring is substituted with the carbon atom of the carbonyl group in its two position. The compounds represented by the above general formula are effective as pesticides and particularly as fungicides, nematocides, miticides, insecticides or herbicides.

The compounds of this invention can be prepared in one or more general reactive steps depending upon the particular compounds desired. When compounds are desired where Y of formula I is hydrogen, then an N-phenyl-hydroxylamine of the formula:

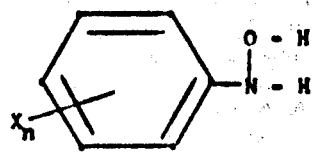

(II)

can be reacted with a furoyl halide of the formula:

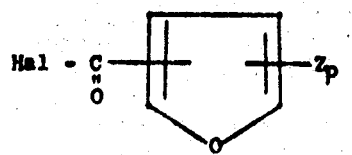

(III)

to form an N-phenyl-N-hydroxy-furancarboxamide represented by formula I where Y is hydrogen. In the formulae II and III, X, n, p and Z have the same significance as for formula I above and Hal is halogen such as chlorine or bromine. For example, X can be halo such as chloro, bromo, iodo, or fluoro; an aliphatic radical such as alkyl of from 1 to about 5 carbon atoms or alkenyl of from 2 to about 5 carbon atoms; nitro; hydroxy; alkoxy where the alkyl portion contains from 1 to 5 carbon atoms; acyl or acyloxy such as saturated or unsaturated acyl or acyloxy containing from 1 to about 5 carbon atoms; and Z can be a halogen; alkyl or alkoxy containing from 1 to about 5 carbon atoms; or nitro. When the compounds represented by formula I are desired having Y other than hydrogen, then an N-phenyl-N-hydroxy-furancarboxamide, prepared as above, can be further reacted to form the compounds represented by formula I having the desired Y substituent. For example, the N-phenyl-N-hydroxy-furancarboxamide of formula II can be further reacted to form compounds of formula I where Y is alkyl and preferably alkyl of from 1 to about 5 carbon atoms; acyl of the formula:

where $R_a$ is an alkyl group of from 1 to about 5 carbon atoms; alkoxycarbonyl or alkylthiocarbonyl of the formula:

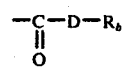

where D is an oxygen or sulfur atom, respectively, and where $R_b$ is alkyl of from 1 to about 5 carbon atoms; alkoxycarbonylalkylene of the formula:

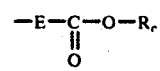

where E is alkylene of from 1 to about 3 carbon atoms and $R_c$ is alkyl of from 1 to about 5 carbon atoms; or a carbamoyl radical of the formula:

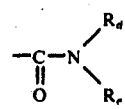

where $R_d$ and $R_e$ are selected from hydrogen, phenyl and alkyl of from 1 to about 5 carbon atoms.

The substituents X, Y and Z of formula I which are illustrated above can also be substituted, where possible, with such groups as halo, hydroxy, alkoxy, acyl, acyloxy, nitro or combinations thereof. For example, X can be haloalkyl, such as chloromethyl, trifluoromethyl; hydroxylalkyl, such as 3-hydroxypropyl; nitroalkyl such as 2-nitroethyl; haloacyl such as trichloroacetyl; Y can be haloalkyl; or haloacyl such as trichloroacetyl. Suitable N-phenyl-hydroxylamines of formula II which can be reacted with a furoyl halide of formula III to form the compounds of formula I where Y is hydrogen include: N-4-chlorophenyl-hydroxylamine, N-3-chlorophenyl-hydroxylamine, N-3,4-dichlorophenyl-hydroxylamine, N-2,4,6-trichlorophenyl-hydroxylamine, N-4-bromophenyl-hydroxylamine, N-4-methylphenyl-hydroxylamine, N-3-methylphenyl-hydroxylamine, N-4-ethylphenyl-hydroxylamine, N-3,4-dimethylphenyl-hydroxylamine, N-4-chloromethylphenyl-hydroxylamine, N-4-trifluoromethylphenyl-hydroxylamine, N-4-hydroxymethylphenyl-hydroxylamine, N-3-nitrophenyl-hydroxylamine, N-4-nitrophenyl-hydroxylamine, N-4-acetylphenyl-hydroxylamine, N-4-trichloroacetylphenyl-hydroxylamine, N-3-formyloxy-phenyl-hydroxylamine, N-4-acetyloxyphenyl-hydroxylamine, N-4-hydroxyphenyl-hydroxylamine, N-3-hydroxyphenyl-hydroxylamine, N-3-methoxyphenyl-hydroxylamine, N-4-ethoxyphenyl-hydroxylamine, N-4-cyanophenyl-hydroxylamine, N-3-chloro-4-methylphenyl-hydroxylamine, or N-3-chloro-4-nitrophenyl-hydroxylamine. Suitable furoyl halides which can be reacted with the above illustrated N-phenyl-hydroxylamines include: 3,5-dichloro-2-furoyl chloride, 4,5-dichloro-2-furoyl bromide, 3,4,5-trichloro-2-furoyl chloride, 3-bromo-2-furoyl chloride, 5-bromo-2-furoyl chloride, 3,4-dibromo-2-furoyl chloride, 5-nitro-2-furoyl chloride, 4-bromo-5-methoxy-2-furoyl chloride, 5-(2-chloroethyl)-2-furoyl chloride, 5-cyano-4-methyl-2-furoyl chloride, 5-ethoxy-2-furoyl chloride, 5-ethoxy-3-furoyl chloride, 4-iodo-3-furoyl chloride, 2,5-dimethyl-3-furoyl chloride, 4-methoxy-3-furoyl chloride, 4-nitro-3-furoyl chloride or 4-ethyl-3-furoyl chloride.

In effecting the preparational reaction of the N-phenyl-hydroxylamine of formula II with the furoyl halide of formula III, the conditions and procedures used can be widely varied. Typically, the reaction can be effected by simply reacting the furoyl halide with the desired N-phenyl-hydroxylamine preferably in the presence of a suitable inert solvent such as dioxane and an acid acceptor such as an alkali metal carbonate or bicarbonate such as sodium bicarbonate. In conducting the reaction it is generally preferred to slowly add a furoyl halide to a mixture of the N-phenyl-hydroxylamine, solvent, and an acid acceptor maintained at a low temperature of about −10° to 5°C. The ratio of the reactants is not usually important and a stoichiometric quantity of the furoyl halide and N-phenyl-hydroxylamine can be suitably used. When the reaction is complete, the desired product can be recovered and purified by conventional techniques including filtration and recrystallization. Examples of the N-phenyl-N-hydroxyfurancarboxamides which can thus be prepared include: N-4'-trichloroacetylphenyl-N-hydroxy-2-furancarboxamide, N-4'-cyanophenyl-N-hydroxy-3,5-dichloro-2-furancarboxamide, N-4'-methylphenyl-N-hydroxy-3,4,5-trichloro-2-furancarboxamide, N-2',6'-diethylphenyl-N-hydroxy-5-bromo-2-furancarboxamide, N-4'-hydroxyphenyl-N-hydroxy-3,4-dibromo-2-furancarboxamide, N-3'-methoxyphenyl-N-hydroxy-5-ethyl-2-furancarboxamide, N-3'-methoxyphenyl-N-hydroxy-5-nitro-2-furancarboxamide, N-4'-chlorophenyl-N-hydroxy-4-iodo-3-furancarboxamide, N-3',4'-dichlorophenyl-N-hydroxy-2,5-dimethyl-3-furancarboxamide, N-4'-bromophenyl-N-hydroxy-5-nitro-3-furancarboxamide, or N-4'-bromophenyl-N-hydroxy-5-chloro-3-furancarboxamide.

As indicated, when the compounds of formula I are desired where Y is other than hydrogen, then an N-phenyl-N-hydroxy-furancarboxamide prepared as described above can be further reacted with a suitable reactant to form the compounds having the desired Y substituent. For example, when Y is to be alkyl, then the reactant employed can be an alkylsulfate where the alkyl portion contains from 1 to about 5 carbon atoms such as dimethyl- or diethyl sulfate; when Y is to be acyl, then the reactant can be an acyl halide containing from 1 to about 5 carbon atoms such as acetyl-, propionyl-, or butyryl chloride; and when Y is to be alkoxycarbonyl or alkylthiocarbonyl, then the reactant can be an alkyl ester of haloformic or halothioformic acids, respectively, where the alkyl portion contains from 1 to about 5 carbon atoms such as methyl-, ethyl-, or propyl chloroformates or chlorothioformates; when Y is alkoxycarbonylalkylene, then the reactant can be a halo substituted acid where the alkoxy portion contains from 1 to about 5 carbon atoms and the alkylene portion contains from 1 to about 3 carbon atoms such as methyl-, propyl-, or butyl α-chloroacetates; and when Y is to be a carbamoyl radical, then the reactant can be an isocyanate or carbamoyl chloride such as methyl-, or ethyl isocyanate, N,N-diphenyl carbamoyl chloride, N,N-dimethyl carbamoyl chloride or N-phenyl carbamoyl chloride.

In preparing the compounds of formula I where Y is other than hydrogen, by reacting the above described reactants with a corresponding N-phenyl-N-hydroxyfurancarboxamide, the procedures and conditions utilized can be widely varied. Typically, however, those procedures and conditions which are conveniently used for O-alkylation or esterification reactions using similar reactants can be suitably utilized. Examples of the compounds of formula I where Y is other than hydrogen which can thus be produced include: N-4'-chlorophenyl-N-methoxy-2-furancarboxamide, N-3'-methyl-phenyl-N-ethoxy-2-furancarboxamide, N-3',4'-diethylphenyl-N-propyloxy-3-bromo-2-furancarboxamide, N-4'-trichloroacetylphenyl-N-butoxy-5-(2-chloroethyl)-2-furancarboxamide, N-4'-methoxyphenyl-N-acetoxy-2-furancarboxamide, N-3',4'-dibromophenyl-N-propionoxy-2-furancarboxamide, N-3',4'-dichlorophenyl-N-butyryloxy-5-cyanomethyl-2-furancarboxamide, N-4'-ethylphenyl-N-acetoxy-5-bromo-2-furancarboxamide, N-2',4'-diisopropylphenyl-N-methoxycarbonyloxy-2-furancarboxamide, N-4'-cyanophenyl-N-ethoxycarbonyloxy-3,4,5-trichloro-2-furancarboxamide, N-3'-formyloxyphenyl-N-methylthiocarbonyloxy-5-nitro-2-furancarboxamide, N-4'-nitrophenyl-N-ethylthiocarbonyloxy-5-methyl-2-furancarboxamide, N-4'-chlorophenyl-N-methoxycarbonylmethoxy-2-furancarboxamide, N-4'-bromophenyl-N-propoxycarbonylmethoxy-4,5-dichloro- 2-furancarboxamide, N-4'-methylphenyl-N-carbamoyloxy-2-furancarboxamide, N-4'-bromophenyl-N-(N'-methylcarbamoyloxy)-3,4-dibromo-2-furancarboxamide, N-2',6'-dimethylphenyl-N-(N',N'-dimethylcarbamoyloxy)-5-ethoxy-2-furancarboxamide, N-3'-nitrophenyl-N-(N-phenylcarbamoyloxy)-3,5-dichloro-2-furancarboxamide, N-4'-chlorophenyl-N-methoxy-4-iodo-3-furancarboxamide, N-4'-bromophenyl-N-acetoxy-2,5-dimethyl-3-furancarboxamide, N-2',6'-dimethylphenyl-N-methoxycarbonyloxy-3-furancarboxamide, N-3'-nitrophenyl-N-methylthiocarbonyloxy-3-furancarboxamide, N-3'-nitro-4-methylphenyl-N-methoxycarbonylmethoxy-4-methyl-3-furancarboxamide, N-3',4'-dichlorophenyl-N-carbamoyloxy-3-furancarboxamide.

The compounds of this invention and the method of preparation therefor can be further illustrated by the following examples.

EXAMPLE 1

N-4'-Chlorophenyl-N-hydroxy-2-furancarboxamide

About 10.0 grams (0.07 mol) of N-4-chlorophenyl-hydroxylamine, 10 grams of sodium bicarbonate, 60 ml. of dioxane and 15 ml. of water were added to a reaction flask. With stirring, 9.7 grams (0.075 mol) of 2-furoyl chloride were slowly added over a period of about 15 minutes with the temperature maintained at about 0° to 5°C. After stirring for about ½ hour, the reaction mixture was combined with ice water. The resultant solids were recovered, water washed, air dried and recrystallized from ethyl acetate to recover 9.6 grams of a pale yellow product having a melting point of 155° to 158°C. Analysis for $C_{11}H_5ClNO_3$:

|  | C | H | Cl |
|---|---|---|---|
| Theoretical %: | 55.63 | 3.39 | 14.92 |
| Found %: | 55.71 | 3.48 | 14.89 |

EXAMPLE 2

N-3'-Nitrophenyl-N-hydroxy-2-furancarboxamide

About 12.0 grams (0.078 mol) of N-3-nitrophenyl-hydroxylamine were reacted with 10.2 grams (0.078 mol) of 2-furoyl chloride according to the general procedure of Example 1 to produce 3.5 grams of a yellow, crystalline product having a melting point of 182° to 185°C. Analysis for $C_{11}H_{18}N_2O_5$:

|  | C | H | N |
|---|---|---|---|
| Theoretical %: | 53.24 | 3.25 | 11.29 |
| Found %: | 53.51 | 3.53 | 11.21 |

EXAMPLE 3

N-4'-Methylphenyl-N-hydroxy-2-furancarboxamide

About 10.0 grams (0.081 mol) of N-4-methylphenyl-hydroxylamine were reacted with 10.6 grams (0.081 mol) of 2-furoyl chloride according to the general procedure of Example 1 to produce 8.7 grams of a white, crystalline product having a melting point of 136° to 137°C. Analysis for $C_{12}H_{11}NO_3$:

|  | C | H | N |
|---|---|---|---|
| Theoretical %: | 66.43 | 5.10 | 6.45 |
| Found %: | 66.46 | 5.25 | 6.42 |

EXAMPLE 4

N-3'-Chlorophenyl-N-hydroxy-2-furancarboxamide

About 15 grams (0.11 mol) of N-3-chlorophenylhydroxylamine were reacted with 16 grams (0.12 mol) of 2-furoyl chloride according to the general procedure of Example 1 to produce 9.2 grams of a white, crystalline product having a melting point of 165° to 167°C. Analysis for $C_{11}H_5ClNO_3$:

|  | C | H | Cl |
|---|---|---|---|
| Theoretical %: | 55.63 | 3.39 | 14.92 |
| Found %: | 55.85 | 3.60 | 14.99 |

EXAMPLE 5

N-3',4'-Dimethylphenyl-N-hydroxy-2-furancarboxamide

About 11.0 grams (0.062 mol) of N-3,4-dimethylphenyl-hydroxylamine were reacted with 10.4 grams (0.080 mol) of 2-furoyl chloride according to the general procedure of Example 1 to produce 9.0 grams of a pale yellow product having a melting point of 128° to 130°C.

EXAMPLE 6

N-3'-Nitro-4'-methylphenyl-N-hydroxy-2-furancarboxamide

About 15 grams (0.089 mol) of N-3-nitro-4-methylphenyl-hydroxylamine were reacted with 11.6 grams (0.089 mol) of 2-furoyl chloride according to the general procedure of Example 1 to produce 15.2 grams of a yellow, crystalline product having a melting point of 169° to 171°C. Analysis for $C_{12}H_{10}N_2O_5$:

|  | C | H | N |
|---|---|---|---|
| Theoretical %: | 54.96 | 3.85 | 10.68 |
| Found %: | 54.71 | 4.35 | 10.64 |

EXAMPLE 7

N-2',6'-Dimethylphenyl-N-hydroxy-2-furancarboxamide

About 10.0 grams (0.073 mol) of N-2,6-dimethylphenyl-hydroxylamine were reacted with 9.6 grams (0.073 mol) of 2-furoyl chloride according to the general procedure of Example 1 to produce 6.0 grams of a white, crystalline product having a melting point of 123° to 124°C. Analysis for $C_{13}H_{13}NO_3$:

|  | C | H | N |
|---|---|---|---|
| Theoretical %: | 67.51 | 5.66 | 6.00 |
| Found %: | 67.23 | 5.85 | 6.10 |

EXAMPLE 8

N-4'-Isopropylphenyl-N-hydroxy-2-furancarboxamide

About 9.5 grams (0.063 mol) of N-4-isopropylphenyl-hydroxylamine were reacted with 8.1 grams (0.063 mol) of 2-furoyl chloride according to the general procedure of Example 1 to produce 8,1 grams of a white, crystalline product having a melting point of 141° to 143°C. Analysis for $C_{14}H_{15}NO_3$:

|  | C | H | N |
|---|---|---|---|
| Theoretical %: | 68.58 | 6.16 | 5.71 |
| Found %: | 68.56 | 6.50 | 5.70 |

EXAMPLE 9

N-3'-Chloro-4'-methylphenyl-N-hydroxy-2-furancarboxamide

About 12.0 grams (0.076 mol) of N-3-chloro-4-methylphenyl-hydroxylamine were reacted with 10.0 grams (0.076 mol) of 2-furoyl chloride according to the general procedure of Example 1 to produce 9.2 grams of a white, crystalline product having a melting point of 141° to 143°C. Analysis for $C_{12}H_{10}ClNO_3$:

|  | C | H | Cl |
|---|---|---|---|
| Theoretical %: | 57.42 | 4.01 | 14.11 |
| Found %: | 57.58 | 4.23 | 14.22 |

EXAMPLE 10

N-3',4'-Dichlorophenyl-N-hydroxy-2-furancarboxamide

About 18 grams (0.10 mol) of N-3,4-dichlorophenyl-hydroxylamine were reacted with 13 grams (0.10 mol) of 2-furoyl chloride according to the general procedure of Example 1 to produce 13.6 grams of a white, crystalline product having a melting point of 167° to 168°C. Analysis for $C_{11}H_7Cl_2NO_3$:

|  | C | H | Cl |
|---|---|---|---|
| Theoretical %: | 48.58 | 2.59 | 26.12 |
| Found %: | 48.37 | 2.59 | 26.38 |

EXAMPLE 11

N-4'-Chlorophenyl-N-methoxy-2-furancarboxamide

About 2.4 grams of N-4'-chlorophenyl-N-hydroxy-2-furancarboxamide (as prepared in Example 1) were charged together with 20 ml. of dioxane, 10 ml. of water, and 2.0 grams of potassium carbonate to a reaction flask. With the temperature about 45°C., 1.7 grams (0.014 mol) of dimethyl sulfate were added over a period of about 5 minutes. The mixture was stirred for about ½ hour and then cooled to about −5°C. Water was added and the resulting solids were recovered and then dissolved in diethyl ether. After drying the resultant solution with magnesium sulfate, the solvent was removed. The residue was then recrystallized from hexane to yield 1.4 grams of a white crystalline product having a melting point of 63° to 65°C. Analysis for $C_{12}H_{10}ClNO_3$:

|  | C | H | Cl |
|---|---|---|---|
| Theoretical %: | 57.42 | 4.01 | 14.11 |
| Found %: | 56.93 | 4.04 | 14.24 |

EXAMPLE 12

N-3'-Nitrophenyl-N-methoxy-2-furancarboxamide

About 10.0 grams (0.040 mol) of N-3'-nitrophenyl-N-hydroxy-2-furancarboxamide (as prepared in Example 2) were reacted with 9.3 grams (0.074 mol) of dimethyl sulfate according to the general procedure of Example 11 to produce 6.2 grams of a tan, crystalline product having a melting point of 101° to 103°C. Analysis for $C_{12}H_{10}N_2O_5$:

|  | C | H | N |
|---|---|---|---|
| Theoretical %: | 54.98 | 3.84 | 10.09 |
| Found %: | 54.69 | 4.17 | 10.41 |

EXAMPLE 13

N-4'-Methylphenyl-N-methoxy-2-furancarboxamide

About 5.0 grams (0.032 mol) of N-4'-methylphenyl-N-hydroxy-2-furancarboxamide (as prepared in Example 3) were reacted with 3.8 grams (0.032 mol) of dimethyl sulfate according to the general procedure of Example 11 to produce 5.5 grams of a white, crystalline product having a melting point of 87° to 89°C. Analysis for $C_{13}H_{13}NO_3$:

|  | C | H | N |
|---|---|---|---|
| Theoretical %: | 67.51 | 5.66 | 6.06 |
| Found %: | 67.51 | 6.13 | 6.02 |

EXAMPLE 14

N-3'-Chlorophenyl-N-methoxy-2-furancarboxamide

About 6.0 grams (0.025 mol) of N-3'-chlorophenyl-N-hydroxy-2-furancarboxamide (as prepared in Example 4) were reacted with 6.0 grams (0.048 mol) of dimethyl sulfate according to the general procedure of Example 11 to produce 4.8 grams of a white, crystalline product having a melting point of 73° to 75°C. Analysis for $C_{12}H_{10}ClNO_3$:

|  | C | H | Cl |
|---|---|---|---|
| Theoretical %: | 57.42 | 4.01 | 14.11 |
| Found %: | 57.30 | 4.37 | 14.02 |

EXAMPLE 15

N-3',4'-Dimethylphenyl-N-methoxy-2-furancarboxamide

About 5.7 grams (0.024 mol) of N-3',4'-dimethylphenyl-N-hydroxy-2-furancarboxamide (as prepared in Example 5) were reacted with 4.3 grams (0.034 mol) of dimethyl sulfate according to the general procedure of Example 11 to produce 4.6 grams of a crystalline product having a melting point of 73° to 75°C. Analysis for $C_{14}H_{15}NO_3$:

|  | C | H | N |
|---|---|---|---|
| Theoretical %: | 68.58 | 6.16 | 5.71 |
| Found %: | 68.32 | 6.22 | 5.73 |

EXAMPLE 16

N-3'-Nitro-4'-methylphenyl-N-methoxy-2-furancarboxamide

About 5.0 grams (0.020 mol) of N-3'-nitro-4'-methylphenyl-N-hydroxy-2-furancarboxamide (as prepared in Example 6) were reacted with 3.2 grams (0.025 mol) of dimethyl sulfate according to the general procedure of Example 11 to produce 4.6 grams of a pale yellow, crystalline product having a melting point of 89° to 92°C. Analysis for $C_{13}H_{12}N_2O_5$:

|  | C | H | N |
|---|---|---|---|
| Theoretical %: | 56.52 | 4.38 | 10.14 |
| Found %: | 56.65 | 4.86 | 9.95 |

EXAMPLE 17

N-2',6'-Dimethylphenyl-N-methoxy-2-furancarboxamide

About 4.4 grams (0.019 mol) of N-2',6'-dimethylphenyl-N-hydroxy-2-furancarboxamide (as prepared in Example 7) were reacted with 3.2 grams (0.025 mol) of dimethyl sulfate according to the general procedure of Example 11 to produce 2.6 grams of a pale orange crystalline product having a melting point of 76° to 78°C. Analysis for $C_{14}H_{15}NO_3$:

|  | C | H | N |
|---|---|---|---|
| Theoretical %: | 68.58 | 6.16 | 5.71 |
| Found %: | 68.87 | 6.57 | 5.51 |

EXAMPLE 18

N-4'-Isopropylphenyl-N-methoxy-2-furancarboxamide

About 5.0 grams (0.020 mol) of N-4'-isopropylphenyl-N-hydroxy-2-furancarboxamide (as prepared in Example 8) were reacted with 3.2 grams (0.025 mol) of dimethyl sulfate according to the general procedure of Example 11 to produce 3.6 grams of product having a melting point of 56° to 58°C. Analysis for $C_{15}H_{17}NO_3$:

|  | C | H | N |
|---|---|---|---|
| Theoretical %: | 69.45 | 6.61 | 5.41 |
| Found %: | 68.98 | 6.70 | 5.31 |

EXAMPLE 19

N-3'-Chloro-4'-methylphenyl-N-methoxy-2-furancarboxamide

About 5.0 grams of N-3'-chloro-4'-methylphenyl-N-hydroxy-2-furancarboxamide (as prepared in Example 9) were reacted with 3.7 grams (0.030 mol) of dimethyl sulfate according to the general procedure of Example 11 to produce 2.9 grams of a white, crystalline product having a melting point of 86° to 88°C. Analysis for $C_{13}H_{12}ClNO_3$:

|  | C | H | Cl |
|---|---|---|---|
| Theoretical %: | 58.84 | 4.56 | 13.41 |
| Found %: | 58.38 | 4.89 | 13.66 |

EXAMPLE 20

N-3',4'-Dichlorophenyl-N-methoxy-2-furancarboxamide

About 6.0 grams (0.023 mol) of N-3',4'-dichlorophenyl-N-hydroxy-2-furancarboxamide (as prepared in Example 10)) were reacted with 3.7 grams (0.030 mol) of dimethyl sulfate according to the general procedure of Example 11 to produce 3.5 grams of a yellow, crystalline product having a melting point of 115° to 117°C. Analysis for $C_{12}H_9Cl_2NO_3$:

|  | C | H | Cl |
|---|---|---|---|
| Theoretical %: | 50.35 | 3.17 | 24.73 |
| Found %: | 49.69 | 3.08 | 24.64 |

EXAMPLE 21

N-4'-Chlorophenyl-N-ethoxycarbonylmethyl-2-furancarboxamide

About 3.6 grams (0.015 mol) of N-4'-chlorophenyl-N-hydroxy-2-furancarboxamide were charged together with 80 ml. of acetone and 2.4 grams of potassium carbonate to a reaction flask. With stirring 2.7 grams (0.017 mol) of ethyl-α-bromoacetate were then added and the mixture heated to reflux and maintained thereat for about 1 hour. The mixture was cooled, and the resultant solids recovered. The acetone was removed under vacuum, and pentane was added to the residue. After removing the pentane, the residue was recrystallized from hexane in the presence of charcoal to yield 4.8 grams of a white, crystalline product having a melting point of 74° to 76°C. Analysis for $C_{15}H_{14}ClNO_5$:

|  | C | H | Cl |
|---|---|---|---|
| Theoretical %: | 55.70 | 4.38 | 10.96 |
| Found %: | 55.67 | 4.46 | 10.98 |

EXAMPLE 22

N-4'-Nitrophenyl-N-hydroxy-5-methyl-2-furancarboxamide

About 12.0 grams (0.078 mol) of N-4-nitrophenylhydroxylamine are reacted with 11.2 grams (0.078 mol) of 5-methyl-2-furoyl chloride according to the general procedure of Example 1 to produce the desired product.

EXAMPLE 23

N-4'-Chlorophenyl-N-hydroxy-5-bromo-2-furancarboxamide

About 10.0 grams (0.07 mol) of N-4-chlorophenylhydroxylamine are reacted with 14.6 grams (0.07 mol) of 5-bromo-2-furoyl chloride according to the general procedure of Example 1 to produce the desired product.

EXAMPLE 24

N-4'-Bromophenyl-N-hydroxy-5-methoxy-2-furancarboxamide

About 18.07 grams (0.1 mol) of N-4-bromophenyl-hydroxylamine are reacted with 16 grams (0.1 mol) of 5-methoxy-2-furoyl chloride according to the general procedure of Example 1 to produce the desired product.

EXAMPLE 25

N-4'-Methylphenyl-N-hydroxy-5-nitro-2-furancarboxamide

About 10.0 grams (0.081 mol) of N-4-methylphenyl-hydroxylamine are reacted with 14.1 grams (0.081 mol) of 5-nitro-2-furoyl chloride according to the general procedure of Example 1 to produce the desired product.

As indiated, the compounds of this invention are useful as pesticides and particularly as herbicides, fungicides, insecticides, nematocides or miticides. As used herein the term pesticide includes herbicide, fungicide, nematocide, insecticide or miticide.

For practical use as pesticides, the compounds of this invention are generally incorporated into pesticidal compositions which comprise an inert carrier and a pesticidally toxic amount of the compounds. Such pesticidal compositions, also defined as formulations, enable the active compound to be applied conveniently, in any desired quantity, to the site of the pest infestation, such as fungus, insect, nematode or mite infestation or to the site of undesired vegetation. These compositions can be solids such as dust, granules, or wettable powders, or they can be liquids such as solutions, aerosols, or emulsifiable concentrates.

For example, dusts can be prepared by grinding and blending the active compounds with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the compounds are sufficiently soluble in common organic solvents such as kerosene or xylene so that they can be used directly dissolved in such solvents. Frequently, these solutions can be dispersed under superatmospheric pressure as aerosols. However, preferred liquid pesticidal compositions are emulsifiable concentrates, which comprise one or more compound according to this invention and as the inert carrier, a solvent and an emulsifier. Such emulsifiable concentrates can be extended with water and/or oil to any desired concentration of the compound for application as sprays to the site of the pest infestation or to the site of the undesired vegetation. The emulsifiers most commonly used in these concentrates are nonionic or mixtures of nonionic with anionic surface-active agents.

A typical pesticidal composition according to this invention is illustrated by the following example, in which the quantities are in parts by weight.

EXAMPLE 26

Preparation of a Dust

Product of Example 1 10
Powdered talc 90

The above ingredients are mixed in a mechanical grinder-blender and are ground until a homogenous, free-flowing dust of the desired particle size is obtained. This dust is suitable for direct application to the site of the pest infestation or to the site of unwanted vegetation.

The compounds of this invention can be applied as pesticides in any manner recognized by the art. One method for destroying pests or undesired vegetation comprises applying to the locus of the pest infestation or the undesired vegetation a pesticidal composition comprising an inert carrier and as the essential active ingredient, in a quantity which is toxic to said pests or to such vegetation at least one of the compounds of this invention. The concentration of the compounds of this invention individually or in admixture in the pesticidal compositions will vary greatly depending on the type of composition and the purpose for which it is designed, but generally the compositions will contain from about 0.05 to about 95 percent by weight of the compounds of this invention. In a preferred embodiment of this invention, the pesticidal compositions will contain from about 5 to 75 percent by weight of the compound. The compositions can also contain additional substances such as other pesticides, stabilizers, spreaders, deactivators, adhesives, stickers, fertilizers, or activators.

When the compounds of this invention are used as insecticides they can be employed in several different ways. When used as stomach poisons or protective material they can be applied to the surface on which the insects feed or travel. When the compounds are used as contact poisons or eradicants they can be applied directly to the body of the insect; as a residual treatment to the surface on which the insect may walk or crawl; or as a fumigant treatment of the air which the insect breathes. In some cases, the compounds applied to the soil or plant surfaces are taken up by the plant, and the insects are poisoned systemically.

The above methods of using insecticides are based on the fact that almost all of the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects such as the Mexican bean beetle, the southern armyworm; the piercing-sucking insects, such as the pea aphid, the cereal leaf beetle, the house fly, the grape leafhopper, the chinch bug, the lygus bugs, oyster shell scale, the California red scale, the Florida red scale, the soft scale and mosquitoes; the internal feeders, including borers such as the European corn borer, the peach twig borer and the corn earworms, worms or weevils such as the codling moth, alfalfa weevil, cotton boll weevil, pink boll worm, plum curculio, red banded leaf roller, melonworm, cabbage looper and apple maggot, leaf miners such as the apple leaf miner, birch leaf miner and beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

Mites and ticks are not true insects. Many economically important species of mites can be controlled by the compounds of this present invention such as the red spider mite, the two spotted mite, the strawberry spider mite, the citrus rust mite, the cattle tick, the poultry mite, the citrus red mite and the European red mite. Chemicals useful for the control of mites are called miticides, while those useful for the control of both mites and ticks are known specifically as acaricides.

The quantity of active compound of this invention to be used for insect control will depend on a variety of factors, such as the specific insect involved, intensity of the infestation, weather, type of environment, type of formulation, and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

When the compounds of this invention are used as agricultural fungicides, they can be applied to plant foliage, to seeds, to the soil, or to such parts of plants as the fruits themselves. Plants are susceptible to a great many diseases which cause widespread damage; and among some of the more important which can be mentioned are late blight on tomato, powdery mildew on cucumber (*Erisiphe cichoracearum*), cereal leaf rust on wheat (*Puccinia rubigo-vera*), and such common soil fungi as fusarium wilt (*Fusarium oxysporum*), the seed rot fungus (*Phythium debaranum*), and the sheath and culm blight (*Rhizoctonia solani*). The new compounds of this invention can also be employed as industrial fungicides to control a variety of fungi which attack such materials as adhesives, cork, paints, lacquers, leather, wood, plastics, and textiles such as cotton and wool.

The quantity of active compound of this invention to be used for good disease control will depend on a variety of factors, such as the particular disease involved, the intensity of the infestation, formulation, weather, type of crop and the like. Thus, while the application of only one or two ounces of active compound per acre of a crop may be sufficient to control a light infestation of certain fungi, a pound or more of active compound per acre may be required to control a heavy infestation of a hardy species of fungus.

When the compounds of this invention are used as nematocides to control or prevent infestations of destructive nematodes, they are ordinarily used as soil treatments. Plant parasitic nematodes occur in enormous numbers in all kinds of soil in which plants can grow, and many plant pathologists believe that all the crop and ornamental plants grown in the world can be attacked by these nematodes. The destructive species of nematodes range from the highly specialized, which attack only a few kinds of plants, to the polyphagous, which attack a great many different plants. The plants almost invariably become infected by nematodes that move into them from the soil. The underground parts of plants, roots, tubers, corns, and rhizomes are thus more apt to be infected than above-ground parts, but infection of stems, leaves, and flower parts is also fairly common.

Damage to plants attacked by nematodes is due primarily to the feeding of the nematodes on the plant tissues. The nematodes may enter the plant to feed, may feed from the outside, or be only partially embedded. The feeding of a nematode may kill the cell or may simply interfere with its normal functioning. If the cell is killed, it is often quickly invaded by bacteria or fungi. If the cell is not killed, it and the adjacent cells may be stimulated to enlarge or multiply. Hence the most common types of nematode damage are manifested as rotting of the attacked parts and adjacent tissue or the development of galls and other abnormal growths. Either can interfere with the orderly development of the plant and cause shortening of stems or roots, twisting, crinkling or death of parts of stems and leaves, and other abnormalities. Consequently, the yield of crop plants is reduced, while a high-quality crop cannot be produced from the crippled plants.

The use of the compounds of this invention for nematode control can make the difference between a good crop and one not worth harvesting. Once the nematodes are controlled, yield increases of 25 to 50 percent are not uncommon. The solid or liquid nematocidal compositions of this invention can be applied to the soil, or in some cases to the plants and soil, in any convenient manner. While broadcast applications to the soil before planting by conventional plow or disc methods are effective, specialized methods such as row placement application, split-dosage applications, postplanting sidedress applications, and the like are also useful. The active compounds of this invention are applied in amounts sufficient to exert the desired nematocidal action. The amount of the active compound present in the nematocidal compositions as actually applied for preventing or controlling nematode infestations varies with the type of application, the particular species which are to be controlled, and the purpose for which the treatment is made.

When the compounds of this invention are used as herbicides, they may be used to destroy undesired vegetation usually referred to as weeds. Weeds, frequently classified as broadleaf or grassy weeds, are undesirable plants which grow where they are not wanted, have no economic value, and interfere with the production of cultivated crops, and the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvet leaf, purselane, barnyard grass, smartweed, knotweed, cocklebur, wild buckwheat, kochia, medic, corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, round-leaved mallow, bull thistle; or perennials such as white cockle, perennial ryegrass, quackgrass, Johnson grass, Canada thistle, hedge bindweed, Bermuda grass, sheep sorrel, curyl dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

The new compounds of this invention are particularly valuable for weed control because they are toxic to many species and groups of weeds while they are relatively non-toxic to many beneficial plants. The exact amount of compound required for herbicides will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The compounds of this invention can be combined with different fungicides, miticides, nematocides, insecticides or herbicides or combinations thereof to form either synergistic pesticide compositions or pesticide compositions capable of more than pesticidal activity. For example, the compounds may be combined with insecticides such as halogenated compounds for example, DDT, methoxychlor, TDE, lindane, chlordane, isobenzan, aldrin, dieldrin, heptachlor, endrin, mirex, endosulfon, dicofol, and the like; organic phosphorus compounds, for example, TEPP, schradan, ethion, parathion, methyl parathion, EPN, demeton, carbonphenothion, phorate, zinophos, diazinon, malathion, mevinphos, dimethoate, DBD, ronnel, oxydemeton-methyl, dicapthon, chlorothion, phosphamidon, naled, fenthion, trichlorofon, or DDVP; organic nitrogen compounds, for example, dinitro-o-cresol, dinitrocyclohexylphenol, DNB, DNP, binapacril, azobenzene, and the like; organic carbamate compounds, for example, carbaryl or ortho 5353, organic sulfur compounds for example phenothiamine, phenoxathin, lauryl thiocyanate, [bis (2-thiocyanoethyl) ether] or isobornyl thiocyanoacetate; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide or paradichlorobenzene, with fungicides such as ferbam, nabam, zineb, ziram, thiram, chloranil, dichlone, glyodin, cycloheximide, dinocap, maneb, captan, dodine, PCNB, or p-dimethylaminobenzenediazo sodium sulfonate; with nematocides such as chloropicrin, O,O-diethyl-O-(2,4-dichlorophenyl) phosphorothioate, tetrachlorothiophene, dazomet, or dibromochloropropane, with miticides such as O,O-diisopropyl-S-(isopropylthiomethyl) phosphorodithioate, O,O-diisopropyl-S-diethyldithiocarbamoyl phosphorodithioate, dimefox, or dimethoate, and with herbicides, defoliants, dessicants or growth inhibitors such as chlorophenoxy herbicides for example, 2,4-D, 2,4,5-T, MCPA, MCPB, 4(2,4-DB), 2,4-DEB, 4-CPB, 4-CPA, 4-Cpp, 2,4,5-TB, 2,4,5-TES, 3,4-DA, silvex and the like; carbamate herbicides for example IPC, CIPC, swep, barban, BCPC, CEPC, or CPPC, thiocarbamate and dithiocarbamate herbicides for example CDEC, metham sodium, EPTC, diallate, PEBC, perbulate, or vernolate; substituted urea herbicides for example norea, siduron, dichloral urea, chloroxuron, cycluron, fenuron, monuron, monuron TCA, diuron, linuron, monlinuron, neburon, buturon, or trimeturon; symmetrical triazine herbicides for example simazine, chlorazine, atratone, desmetryne, norazine ipazine, prometryn, atrazine, trietazine, simetone, prometone, propazine, or ametryne; chloroacetamide herbicides for example alpha-chloro-N,N-dimethylacetamide, CDEA, CDAA, alphachloro-N-isopropylacetamide, 2-chloro-N-isopropylacetanilide, 4-(chloroacetyl) morpholine, or 1-(chloroacetyl) piperidine; chlorinated aliphatic acid herbicides for example TCA, dalapon, 2,3-dichloropropionic acid, or 2,2,3-TPA, chlorinated benzoic acid and phenylacetic acid herbicides for example 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, or 2,5-dichloro-3-aminobenzoic acid; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil; DPA, diphenamid, dipropalin, trifluralin, solan, dicryl, merphoa, DMPA, o-S-dimethyl tetrachlorothioterephthalate, methyl 2,3,5,6-tetrachloro-N-methoxy-N-methyl-terephthalamate, 2-[(4-chloro-o-tolyl)-oxy]-N-methoxyacetamide, DSMA, MSMA, potassium azide, acrolein, benefin, bensulide, AMS, bromacil, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-632, M-2901, planavin, sodium tetraborate, calcium cyanamide, DEF, ethyl xanthogen disulfide, sindone, sindone B, or propanil.

The pesticidal activity of the compounds of this invention may be illustrated by the following examples.

EXAMPLE 27

The fungicidal activity of the compounds of this invention can be demonstrated by the following tests:

An emulsifiable concentrate containing the test compound at a rate of 25 mg. per ml. was prepared by dissolving the compound in a suitable solvent such as acetone containing a surface active agent (polyoxyalkylene derivatives of sorbitan monolaurate and/or monooleate, 2.48 mg. per 80 ml. of acetone).

The compounds were used to control the fungi, *Rhizoctonia solani* and *Fusarium oxysporum* by first preparing an aqueous fungicidal composition by admixing 1 ml. of the above emulsifiable concentrate with 77 ml. of water. Two series of soil samples were prepared by placing about 100 ml. of soil into paper cups. In each series the soil had been inoculated with one of the respective fungi which had been obtained from cultures ranging in age of about 10 to 14 days. A portion of the soil samples in each series was treated by drenching the soil in the cups with the fungicidal composition in an amount sufficient to provide an application rate equivalent to 100 pounds of the compound per one acre having a depth of 4 inches. The other portion of the soil samples in each series was not so treated and was used for comparative purposes. All of the cups were then sealed and stored under conditions favorable to fungus growth for a period ranging from about 2 to 4 days. At the end of the period, the cups were opened and the growth on the surface of the soil was observed. The growth of the fungus on the surface of the treated samples was rated in comparison to the growth on the untreated samples on a percentage basis of the ability of the test compound to control or retard fungus growth. The results of the test were as follows.

| Test Compound | Percent Control | |
|---|---|---|
| | Rhizoctonia solani | Fusarium oxysporum |
| N-3'-chlorophenyl-N-methoxy-2-furancarboxamide | 71.7 | 51.7 |

The compounds were used to control the fungus *Puccinia rubigo-vera* (leaf rust of wheat) by first preparing an aqueous fungicidal spray composition by admixing the above prepared emulsifiable concentrate with sufficient water to provide the desired concentration of the test compound. A series of 6 day old Henry wheat plants were treated with the compounds by spraying the composition for a period of about 30 seconds at a spray pressure of 80 pounds per square inch. Another series of plants were not so treated and were used for comparative purposes. After the treated plants had dried, both the treated and untreated plants were inoculated with a 9 to 13 day old culture of the fungus. The plants were then stored under conditions favorable to fungus growth for a period of 8 days. At the end of the period the plants were examined to determine the extent of fungus growth. The extent of the fungus growth in the treated plants was compared to that of the untreated plants and was rated on a percentage basis of the ability of the compounds to retard fungus growth. The results of the test were as follows:

| Test Compound | Concentration; Parts Per Million by Weight | Percent Control |
|---|---|---|
| N-4'-methylphenyl-N-methoxy-2-furancarboxamide | 1000 | 46.7 |

The compounds were used to control the fungus *Erysiphe cichoracearum*, powdery mildew of cucumber by first preparing an aqueous composition as above having the desired concentration of the test compound. Susceptible species of cucumbers were grown in soil contained in plastic pots having 2 to 3 plants per pot. After the cucumber plants were 10 to 14 days old they were sprayed with the fungicidal composition. Another series of the plants was not sprayed and was used for comparative purposes. After the sprayed plants had dried each plant in both series was surrounded by 3 plants infested with the fungus. After 9 to 14 days the extent of disease was observed and rated in comparison with the untreated plants. The results of the test were as follows:

| Test Compound | Concentration; Parts Per Million by Weight | Percent Control |
|---|---|---|
| N-3'-chlorophenyl-N-methoxy-2-furancarboxamide | 1000 | 87.5 |
| N-3'-chlorophenyl-N-hydroxy-2-furancarboxamide | 1000 | 57.5 |

The compounds were used to control the fungus *Phytophthora infestans* (late blight of tomato). An aqueous fungicidal composition was first prepared as above to provide the desired concentration of the test compound. Susceptible species of the tomato plants grown in individual paper pots were sprayed with the pesticidal composition when they had grown to a height of approximately 6 to 8 inches. A number of the plants were not sprayed and were used for comparative purposes. After the sprayed plants had dried, both series of plants were sprayed with a suspension of the fungus spores which had been reared on lima bean agar. After a few days to one week, the disease symptoms in the treated plants were observed and rated in comparison to the untreated plants. The results of the test were as follows:

| Test Compound | Concentration; Parts Per Million by Weight | Percent Control |
|---|---|---|
| N-4'-isopropylphenyl-N-hydroxy-2-furancarboxyamide | 1000 | 92.0 |

EXAMPLE 28

The nematocidal activity of the compounds of this invention can be demonstrated by the following test:

One of the compounds was used to control rootknot nematodes. A sample of inoculated soil was prepared by mixing 1 part of sand, 4 parts of sterilized soil and 3 parts of soil from a 4 month old rootknot nematode culture. The soil sample prepared as above was placed in 4 inch plastic pots and manually compacted. An aqueous nematocidal composition was prepared by admixing the emulsifiable concentrate as prepared in Example 23 with water. The soil in one series of the pots was treated by drenching the soil in each pot with a quantity of the nematocidal composition sufficient to provide the desired concentration of the test compound in the soil. The other series of the pots was not so treated and was used for comparative purposes. Both series of pots were placed in a greenhouse and held for 7 days whereupon 10 to 14 day old tomato seedlings (Bonny Best) were planted in the pots. After about 2 weeks, the degree of nematode control was evaluated by comparing the number of rootknot nematode galls on the roots of the plants grown in the treated soil with the number of galls on the plants grown in the untreated soil. The results of the test were as follows:

| Test Compound | Concentration; lb/acre of 4" in Depth | Percent Control |
|---|---|---|
| N-3',4'-dichlorophenyl-N-hydroxy-2-furancarboxamide | 100 | 93.5 |

EXAMPLE 29

The insecticidal activity of the compounds of this invention can be demonstrated by the following tests:

N-4-isopropylphenyl-N-methoxy-2-furancarboxamide was used to control insects according to the following test procedures. An insecticidal spray composition was prepared by admixing the emulsifiable concentrate as prepared in Example 23 with sufficient water to provide a weight concentration of 3500 ppm of the test compound.

Southern armyworms [*Prodenia eridania*(cram)] were controlled by spraying lima bean leaves with the insecticidal composition and offering the sprayed leaves to armyworm larvae (third instar stage) for feeding. After 48 hours, it was observed that the mortality rate of the larvae was 60 percent.

Mexican bean beetles (*Epilacina baribespis*) were controlled by offering lima bean leaves which had been dipped in the insecticidal composition to bean beetle larvae (third instar stage) for feeding. After 48 hours, it was observed that the mortality rate of the larvae was 50 percent.

EXAMPLE 30

The herbicidal activity of the compounds of this invention can be demonstrated by the following tests:

A herbicidal composition containing the test compound was first prepared by admixing the emulsifiable concentrate as prepared in Example 23 with water, and was used in the pre-emergence control of different species of plants as follows. Small plastic pots filled with dry soil were seeded with the plant species to be controlled. After 24 hours after seeding, the pots were sprayed with water until the soil was wet. Then the soil was treated with the herbicidal composition by spraying the soil to provide the desired application rate of the test compound. After spraying, the pots were placed in a greenhouse under favorable growth conditions. After a period of about 15 to 21 days the condition of the plants and the degree of injury to the plants were rated on a scale of 0 to 10 as follows: 0 = no injury; 1, 2 = slight injury; 3, 4 = moderate injury; 5, 6 = moderately severe injury; 7, 8, 9 = severe injury; 10 = death. The results of the test were as follows:

| Test Compound | Plant Controlled | Application Rate of Test Compound lb/acre of 4" Depth | Injury Rating |
|---|---|---|---|
| N-3'-nitrophenyl-N-hydroxy-2-furan-carboxamide | Downy Brome | ½ | 10 |
| | Ryegrass | 4 | 10 |

EXAMPLE 31

The miticidal activity of the compounds of this invention can be demonstrated by the following test:

N-4'-isopropylphenyl-N-methoxy-2-furancarboxamide was used to control two spotted spider mites [*Tetranychus urtices* (Koch)]. A miticidal composition was prepared by mixing the emulsifiable concentrate as prepared in Example 23 with a quantity of water sufficient to provide a concentration of 3500 ppm by weight of the test compound. This miticidal composition was then applied to a number of plants which were infected with a predetermined number of the mites. The plants were then stored for five days at which time it was observed that the mortality rate of the mites was 85 percent.

We claim:

1. A herbicidal composition comprising an inert carrier and, in a herbicidally toxic amount, at least one compound of the formula

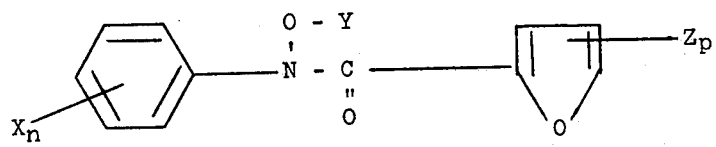

wherein $n$ is an integer of from 1 to 3; X is selected from the group consisting of halogen, alkyl or alkenyl of from 1 to 5 carbon atoms, nitro, hydroxy, alkoxy of from 1 to 5 carbon atoms,

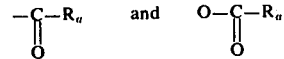

where $R_a$ is an alkyl group of from 1 to 5 carbon atoms and cyano; Y is selected from the group consisting of alkyl of from 1 to 5 carbon atoms,

where $R_a$ is an alkyl group of from 1 to 5 carbon atoms, alkoxycarbonyl, wherein the alkoxy group is from 1 to 5 carbon atoms, alkylthiocarbonyl wherein the alkyl group is from 1 to 5 carbon atoms, alkoxycarbonylalkylene, wherein the alkoxy and alkylene groups are from 1 to 5 carbon atoms, and carbamoyl; Z is selected from the group consisting of halogen, alkyl of from 1 to 5 carbon atoms, alkoxy of from 1 to 5 carbon atoms and nitro; and $p$ is an integer of from 0 to 3.

* * * * *